United States Patent [19]

Strobel et al.

[11] Patent Number: 5,322,779
[45] Date of Patent: Jun. 21, 1994

[54] TAXOL PRODUCTION BY TAXOMYCES ANDREANAE

[75] Inventors: Gary A. Strobel, Bozeman; Andrea A. Stierle; Donald B. Stierle, both of Butte, all of Mont.

[73] Assignee: The Research and Development Institute, Inc. at Montana State University, Bozeman, Mont.

[21] Appl. No.: 971,508

[22] Filed: Nov. 4, 1992

Related U.S. Application Data

[63] Continuation-in-part of Ser. No. 869,726, Apr. 16, 1992, abandoned.

[51] Int. Cl.$^5$ ............... C07D 305/00; C07D 407/00; C12N 1/14; C12P 17/02
[52] U.S. Cl. .................................. 435/123; 435/117; 435/132; 435/147; 435/155; 435/171; 435/254.1; 435/911; 549/510; 549/511
[58] Field of Search ............... 435/123, 117, 132, 147, 435/155, 171, 254.1, 911; 549/510, 511

[56] References Cited

U.S. PATENT DOCUMENTS 4,206,221 6/1980 Miller et al. .................. 424/278
4,468,458 8/1984 Sato et al. ..................... 435/134
5,019,504 5/1991 Christen et al. ............... 435/123

Primary Examiner—Douglas W. Robinson
Assistant Examiner—L. Blaine Lankford
Attorney, Agent, or Firm—Lowe, Price, LeBlanc & Becker

[57] ABSTRACT

Taxol is produced from a taxol-producing microorganism Taxomyces andreanae CBS 279.92. Radioactive taxol products and methods for use of the radioactive labelled taxol are described.

9 Claims, 9 Drawing Sheets

TAXOL PRODUCTION BY TAXOMYCES ANDREANAE

This is a continuation in part of U.S. application Ser. No. 07/869,726, filed Apr. 16, 1992 now abandoned.

TECHNICAL FIELD

The present invention relates to the use of one or more microorganisms to produce taxol (and related taxanes). The invention discloses the rationale for the discovery of said microorganisms, their isolation, screening for taxol production, growth requirements taxol production, and chemical evidence for taxol. (taxane) production.

BACKGROUND OF THE INVENTION

Taxol, which is of the chemical structural formula:

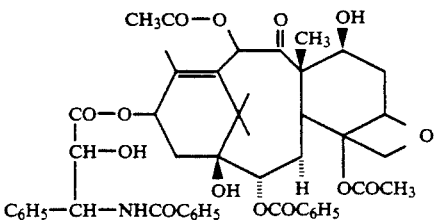

shows significant properties of promoting the polymerization of tubulin and inhibiting the depolymerization of microtubules. For these reasons, taxol is a valuable antileukemic and antitumor agent and is the subject of increasing research.

Taxol is known to be extracted from the trunk bark of different species of the Taxus, or Yew tree. Yields are generally low, usually on the order of no more than about 100 milligrams per kilogram in the extraction process. Various procedures for the production of taxol are known for example, from U.S. Pat. Nos. 4,814,470 and 4,857,653. A chemical process for the preparation of taxol is disclosed in U.S. Pat. No. 4,924,011.

Wani et al, "Journal of the American Chemical Society", Vol. 93, May 1971, No. 9, pages 2325-2327, reports on the structure of taxol and its potential use as an antileukemic and tumor inhibitory compound. This publication further discusses an alcohol extraction procedure for obtaining taxol from the stem bark of the western Yew tree (*Taxus brevifolia*).

The Pacific yew, *Taxus brevifolia*, is one of ten Taxus species known worldwide. It is not confined to the Pacific coast of North America as its name might imply, but grows inland as far east as Glacier National Park, Mont. Generally, it is a small tree, 7-13 meters in height and 5-10 cm in diameter. The crown large and conical. Commonly, however, it is contorted with the main stem and some of the lower limbs growing close to the ground producing numerous adventitious roots resulting in a complex and dense interwoven thicket of growth. The tree is usually associated with deep, rich, moist soils near streams and lakes. It is an understory tree commonly found with Douglas fir, Western hemlock, Western red cedar and Western latch.

The inner bark of this remarkable little tree is the primary source of taxol. Taxol is a highly derivatized terpenoid having the structure indicated above, and has shown remarkable promise as an anti-tumor agent especially in breast and ovarian cancers. Unfortunately, at the present time, the supplies of taxol are inadequate to meet the current or projected demands. Thus, it is essential to understand how, where, and when, taxol is biosynthesized in the tree and the factors that affect its biosynthesis.

It is likely that many factors influence the production of taxol by Pacific yew. These include not only various environmental factors such as temperature and moisture level, but the genetic background of the tree itself. Also, plants are commonly hosts to a multitude of microbes including parasites, symbionts, endophytes, epiphytes, and mycorrhizal fungi. These organisms may also influence the production of secondary plant metabolites such as phytoalexins, whose presence can be triggered by elicitors from microbes. Such microbes may catabolize or derivatize plant compounds.

These and other reasons prompted the present inventors to devise an "in vitro" system of taxol production (see related U.S. patent application Ser. No. 07/845,097, filed Mar. 3, 1992. The system utilizes isotopic precursors of taxol, an optimized environment and the appropriate plant parts where is synthesized. The result was an "in vitro" system taxol synthesis from the most productive tissue portions of the Pacific yew tree.

However, the above in vitro synthesis described in related application 07/845,097 has certain limitations. The source of taxol production, the Pacific yew, is a relatively rare tree, and there is concern that the supply of taxol is not adequate to meet the demand.

Moreover, other methods, including total chemical synthesis, and derivatization of taxotere to yield taxol are both inadequate. The chemical synthesis methods are multi-stepped and totally non-economically feasible while the taxane derivatization method utilizes a taxane isolated from yew needles.

Clearly, a microbial source of taxol would be preferable if it could be easily grown, would produce taxol (or a related taxane), and utilize the enormous U.S. biotechnology industry fermentation capabilities.

SUMMARY OF THE INVENTION

Accordingly, it is an object of the present invention to provide an improved process for producing taxol, using a taxol producing microbe followed by separation of taxol from the growth medium and/or microbe.

In a further embodiment of the invention, there is provided a radioactive labelled taxol product and methods for use of the radioactive labelled taxol. The labelled taxol can be produced by use of a labelled precursor as described herein. Radiolabelled taxol is a new compound for the present invention and related application 07/845,097 (which produces the labelled taxol by a different process). Because of its radiolabel, it and its derivatives can be identified in the mammal body so one can determine how it functions as an antileukemic and antitumor agent. The taxol may be labelled with any label (stable or unstable) including $^{14}C$, $^{13}C$, tritium ($^3H$) or with $^{15}N$.

STATEMENT OF THE INVENTION

The present invention provides an improved process for producing taxol, which uses a taxol producing microorganism followed by separation of taxol from the growth medium and/or microorganism. One aspect of the invention is a method for isolating a microorganism which produces a taxane, which comprises (a) obtaining tissue fragments from a tree of the Genus Taxus, (b) placing said tissue fragments on agar medium until fungal growth occurs e.g., about 2-5 days, (c) placing fungal hyphae from said fungal growth on mycological agar, and replacing said fungal hyphae on said mycological agar if necessary, until a culture in pure form is obtained, (d) transferring said fungal hyphae to a fungal lab growth medium, with subsequent growth of the fungal culture, (e) removing at least a portion of the culture media containing the fungal culture, thoroughly grinding the mycelium, and adding a chromatographic solvent to the mixture, (f) obtaining a chromatograph of said fungal culture in said solvent, (g) checking the solution for the taxane reaction, e. g. , with vanillin-sulfuric acid spray, and comparing the chromatograph with one or more taxane standards such as taxol, baccatin, cephalomannine, and optionally (h) discarding the cultures which do not produce taxol.

Preferred members of the Genus *Taxus* are *Taxus brevifolia*, *Taxus baccata*, *Taxus cuspiduta*, *Taxus canadensis*, and *Taxus floridana*. Particularly preferred is *Taxus brevifolia*.

The present invention further provides a class microbes which have taxol-producing characteristics. Montana BA, the characteristics of which are described in detail below, is representative of such microbes. The microbes according to the present invention produce taxol in culture. Preferred taxol-producing microbes are fungi, and particularly preferred is a taxol producing fungi isolated from a yew tree. Even more preferred is a fungus designated Montana BA. The present invention provides the major discovery of microbes which will produce taxol. The invention covers any microbe which has taxol producing characteristics. The specific microbes described are considered representative only.

Also, the present invention comprises a taxane composition obtained by culturing a microbe. Preferred is a taxane of the species taxol. Particularly preferred is a taxol composition produced by a microbe, e.g., a fungus having the taxol-producing characteristics of Montana BA.

In another aspect, the present invention provides; a radiolabelled taxane composition obtained by culturing a microbe. Preferred is a radiolabelled taxol composition produced by a microbe which is a. fungus. Even more preferred is a labelled composition produced by a microbe which is a fungus having the characteristics of Montana BA. Particularly preferred labels are $^{14}C$, $^{13}C$, $^{3}H$, or $^{15}N$.

The present invention provides an improved method for producing a bulk pharmaceutical composition, which contains a pharmaceutically effective amount of a taxol composition, combined with one or more pharmaceutically acceptable inert or physiologically active diluents or adjuvants.

Also provided is a pharmaceutical composition, which contains a pharmaceutically effective amount of a radiolabelled taxol composition, as described above, combined with one or more pharmaceutically acceptable inert or physiologically active diluents or adjuvants.

Moreover, the present invention includes a method for the treatment of leukemia or tumors which comprises administering a pharmaceutical composition containing taxol as described above.

In yet another aspect, the present invention provides a method for producing a taxane, which comprises a) exposing a taxane producing microbe according to the present invention as described above to a nutrient media capable of supporting growth of the microbe, b) providing culturing conditions for the media containing the microbe, which conditions are capable of producing growth and reproduction of the microbe, and c) isolating or concentrating the desired taxane from said culture media or said microbe.

Preferred is a method for producing a taxol composition wherein the microbe has the taxol-producing characteristics of Montana BA. More preferred is such a method wherein the microbe is a taxol producing fungi. Further preferred is a method wherein the microbe is isolated from a yew tree.

Also preferred is a method for producing a taxane, as described above, wherein the nutrient media comprises benzoic acid, a benzoic acid metabolite precursor, or a salt of benzoic acid, such as sodium benzoate. Particularly preferred is a method as de scribed above for producing the taxane, wherein the taxane is taxol.

A preferred method for producing a taxane comprises a) exposing a taxol producing microbe to a nutrient media capable of supporting growth of said microbe, b) providing culturing conditions for said media containing said microbe, which are capable of producing growth and reproduction of said microbe, and c) isolating or concentrating said taxane from said culture media or said microbe.

Also preferred is a method for producing a taxane which comprises a) exposing a taxol producing microbe of the invention to a nutrient media capable of supporting growth of said microbe, wherein said media contains benzoic acid, b) providing culturing conditions for said media containing said microbe, which conditions are capable of producing growth and reproduction of said microbe, and c) isolating or concentrating said taxane from said culture media or said microbe.

In another preferred aspect of the present invention provides a method for producing a taxol which comprises a) exposing a taxol producing .microbe of the invention to a nutrient media capable of supporting growth of said microbe, wherein said media contains benzoic acid, b) providing culturing conditions for said media containing said microbe, which conditions are capable of producing growth and reproduction of said microbe, and c) isolating or concentrating said taxol from said culture media or said microbe.

Figure 1:
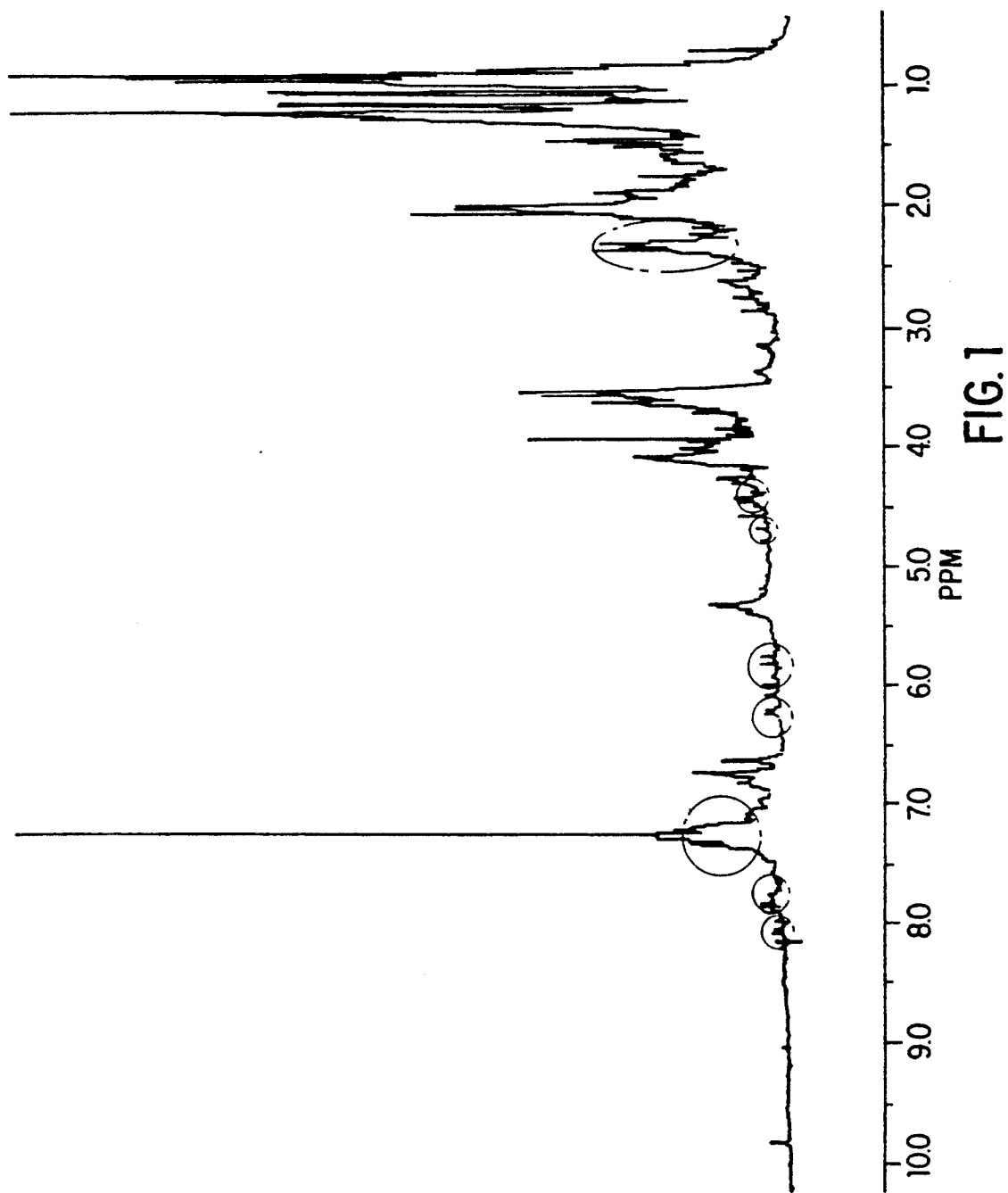
FIG. 1 shows the NMR spectrum of a semi-purified culture extract from Montana BA fungus.

FIG. 9 shows the transmission electron micrograph of *T. andreanae* bulbil cells at a higher magnification. Note that the cell wall has two distinct layers, and a fibrous material between the cells; Bar=1 μm.

DESCRIPTION OF THE INVENTION

All land plants serve as life support systems to a host of microbes. The microbes exist as parasites saprophytes, endophytes, symbionts or mycorrhizae. On occasion, there may be intergeneric exchange of genetic information between one or more of these organisms and its hosts, or vise versa. With the former case, it well documented that certain species of agrobacteria are capable of genetically transforming their host plants via either the Ri or Ti plasmids. The result is that a genetically altered plant is formed that has one or more characteristics of the agrobacterium.

Numerous cases are known in which all phytohormones, known throughout the plant kingdom, are also produced by one or more plant parasitic bacteria or fungi. These include indole acetic acid, the gibberillins, some cytokinins, abscissic acid and ethylene. Recently, the present applicants have also shown that certain terpenoids that were originally thought to be exclusively higher plant associated compounds, are also produced by a plant pathogenic fungus ( See, Bunkers et al. , "Production of Petasol" Mycol. Res 95, (3); 347–351 (1991)).

Thus, while there is no published evidence that taxol could or would be produced by any microorganism, the present applicants explored the microorganism option—the rationale being, that taxol (taxanes) may be produced by one or more microbes associated with the yew tree.

Logically the basis for this concept is that microbes exists which will produce taxol because genetic exchange previously occurred, either between the microbe(s) (as original source of taxol) or yew (as original source of taxol). The net result would be the most desirable case of possessing one or more microbes which could be placed in fermenters to produce taxol.

The present invention provides a method for locating and isolating microorganisms which produce taxol, and provides specific examples where such taxol producing organisms are found. Other microorganisms associated with the yew or related trees, which produce taxol or related taxanes, may be isolated using the present method. Therefore, the present invention considered to be inclusive of all such microbes.

One method of the invention involves finding, isolating and characterizing one or more microbes from yew forests or elsewhere which produce taxol (taxanes). The most logical place to focus the search for such an organism is in one or more locations which have naturally supported the growth of yew trees for centuries.

After locating the yew tree, the following general method is followed to isolate microbes which produce taxol.

Small stems were cut from the yew tree, treated with 70% ethanol as a disinfectant and then, with a sterile blade, removing the outer bark. Pieces of the inner bark of the stem, which is enriched with taxol (Wani's paper), are then placed on agar medium (water agar) until fungal growth occurs after 2–5 days. Then, tips of the fungal hyphae are removed from the water agar and subsequently placed on mycological agar. The culture is obtained in a pure form as judged by its behavior on the plate. Lab contaminants seldom occur due to the rigor of the aseptic technique which was used.

Once the organism is obtained in a pure form it is ultimately transferred to one or more lab media. In this case the modified M-1-D medium (Table 1, below") with yeast extract is used to support the growth of the microbe. Alternatively, (Table 2, below) another medium which resembles the soluble sugars (quantity and quality) of the yew bark, plus a mixture of amino acid (or critical amino acids and another nitrogen source, such as ammonium salts), Na benzoate and acetate are included.

The incubation of the fungus is carried out at 25° C. (in 100 ml of medium in a 250 ml flask, for example) under-still conditions (occasionally shake periodically—every other day, for example) for 3 weeks. At the end of the incubation period the fluid (media) is decanted and the mycelium is thoroughly ground (disrupted) at maximum speed in a Sorvall Ominimixer for 30 sec. Then, an equal volume of chloroform methanol solution 10:1 v/v is added to the medium and ground fungal mycelial solutions. The chloroform layer (bottom) is removed in a separatory funnel. The process may be twice repeated. Ultimately, the chloroform layers are collected together and subjected to flash evaporation under a vacuum at 35°–40° C. until dry.

A portion of the residue is then chromatographed on a 5×10cm plate of silica gel in solvent B (below) (Merck silica gel 0.25 mm). Authentic standards of taxol, baccatin, and cephalomannine are also chromatographed for comparison.

The standard solvents used in the chromatographic procedures are:

A) chloroform/methanol 7:1 V/V

B) chloroform/acetonitrile 7:3 V/V

C) ethyl acetate/isopropanol 95:5 V/V

D) methylene dichloride/tetrahydrofuran 6:2 V/V.

The taxanes (taxol, baccatin, cephalomannine) all absorb short wave UV light (254 angstroms) and react with the vanillin-sulfuric acid spray (see, Cardellina, J. Liquid Chromatography 14: p 6659–665 (1991) to produce an intense blue coloration fading to gray then turning brown after 24 hours.

Each fungus culture was treated in the same manner. At least 50 fungi and 10 bacteria were isolated from yew roots, needles, stems, or fruits and tested. Samples of the extract from each organism were subjected to initial screening by TLC in solvent A.

A few microbes appeared promising after the initial screening. That is, their extract produced blue spot at $R_f$ 0.75–0.81 in solvent A (same as taxol). These microbes were fungi and one later identified as *Cladosporiummacrocarpum*, was further checked for taxol by other methods—but without success. A strain of fungus, designated Montana BA, exhibited several important absorbances in HNMR consistent with the spectrum of taxol (see FIG. 1). Therefore, this culture held promise for taxol production and was studied further. The following are descriptions of the fungus and taxane production.

(1) Montana BA—rapidly growing on potato dextrose agar, most hyphae with growth oppressed to agar surface, no apparent fruiting structures, beige coloration of hyphae. (Culture on deposit).

(2) Evidence for taxol (taxane) production (a) The fungus was grown in both M-1-D and Taxol Microbial culture medium (2 liters) for 3 weeks at 25° C. with only periodic shaking. The medium and the grown mycelium were extracted with chloroform:MeOH 10:1 v/v.

After evaporation of the chloroform:MeOH the residue was taken up in 0.5 ml of $CHCl_3$ MeOH 10:1 v/v and subjected to preparative TLC in solvent B on Merck plates 0.5 mm (20×20). A band at $R_F$ 0.47–0.50 that had slight UV (254 angstroms) absorbance and gave a slight reaction with the vanillin sulfuric acid spray was scraped from the plate and eluted with acetonitrile.

Figure 2:
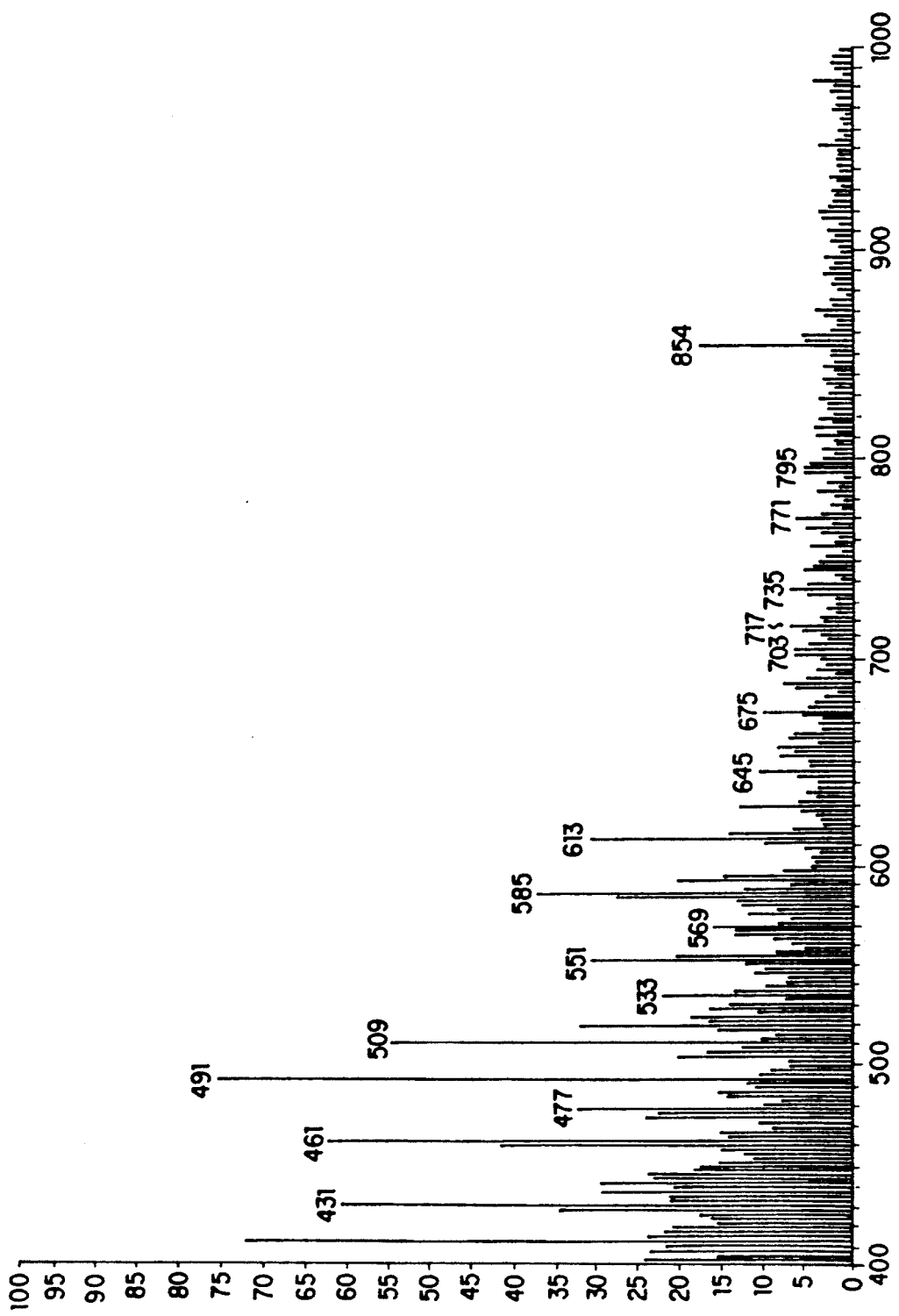
FIG. 2 shows a FAB mass spectrum of taxol obtained by culturing the Montana BA fungus.

Further chromatography was done in solvent A in TLC (precleaned plates with the same solvent). The "taxol" band was eluted and subjected to spectroscopy. This band had the same FAB mass spectrum as authentic taxol with an $M^{+1}$ at 854 and prominent peaks at 491, 509 and 613 (see FIG. 2).

The UV spectrum of the compound had an absorption maximum at 273 nm which is identical to authentic taxol (see Wani et al). The NMR spectrum of the semipurified compound possessed all of the major absorbances of authentic taxol (FIG. 1).

In addition, the $R_F$ values for the taxol preparation from the fungus "Montana BA" was identical to authentic taxol (see Table 3 below).

It is also to be noted that the compound "baccatin", a taxane related to taxol, also appeared in the fungal extract. It, along with taxol, yielded the same intense blue color reaction and the same UV (254) absorption properties as the authentic compounds. It also had the same $R_F$s as authentic baccatin (Table 3).

The amount of taxol per liter (3 wk old culture) is estimated at about 1–2 μg. Baccatin appears at level of 0.5–1 μg/liter.

The taxonomy and properties of the microbe revealed a fungus of the family *Fungi imperfecti* (or alternatively called the family Hyphomyces). The genus was determined to be Taxomyces and the species was named andreanae.

*T. andreanae* (Montana BA) may be related to Oidium, Rhinotrichum, or Monilia by virtue of the similarity of conidial shape, color (hyaline) and the basipetal manner of conidial formation. However, it differs from these organisms since it forms the bulbil or sterile cell masses which appear to be unique structures.

Type species: *Taxomyces andreanae* Strobel, Stierle, & Hess.

Holotypus: Based on material taken from the bark of *Taxus brevifolia* Nutt., infested living bark samples. Agar slants containing the type are deposited with the Montana State University (MSU) mycological collection, D. E. Mathre, Department of Plant Pathology, Montana State University—col. no. 738 Duplicate cultures are deposited at the Centraalbureau Voor Schimmelcultures, Oosterstratt 1, P.O. Box 273, 3740AG, Netherlands CBS, Baarn, Holland 25 culture 279.92 deposited Jun. 1, 1992.

A pure culture species was obtained of Montana BA which was named *Taxomyces andreanae* S1. Two further fungel cultures, other than Montana BA, which produced taxanes were obtained from the above screening. Their characteristics revealed them to be of the same genus and species, but to have slightly different properties. These microbes were isolated to pure culture form and given the names *Taxomyces andreanae* 52 and *Taxomyces andreanae* 53, respectively. Further details are presented below in the experimental section.

(b) To dispel the notion that the taxol isolated from the culture medium might be occurring as a result of the fungus's previous association with the yew tree, the fungus "plugs" used to inoculate the medium were exhaustively extracted and the residue chromatographed. There was no evidence of taxol.

(c) In order to be assured that taxol is produced "de novo" by the fungus, the fungus was incubated for 3 weeks in two 500 ml cultures of Taxol Microbial Culture medium and added 100 μCi of NaAC-1- $^{14}C$ (54 mCi/mole) plus 125 μCi of mixed amino acids 1.75 mCi/mg. Both the taxol and baccatin areas on the preparative TLC's were isolated and then subjected on 2 plates to 3 dimensional TLC (20×20 plate—25 mm layer) along with (co-chromatography) authentic taxol and baccatin. The UV absorbing spot was removed by scraping and counted by liquid scintillation methods. The results show that the area on the plates having radioactivity was identical to the UV absorbing spot. This was true on both taxol and baccatin. This test assures that both baccatin and taxol were synthesized 'de novo' by the fungus.

Throughout the course of the taxol microbial study, there was needed a means of determining the cytotoxicity of the culture extracts and various column fractions to facilitate bioassay guided fractionation. Ferrigni et al., J. Nat. Prod. 45, 679 (1982); and Ferrigni et al., J. Nat. Prod. 47, 347 (1984), suggested that a simple brine shrimp assay provided reasonable facsimile of the standard anticancer assays. Those authors were able to isolate the antileukemic principles from the seeds of *Euphorbia lagascae* Spreng using a fractionation scheme guided by brine shrimp and potato disc assays. Several studies have demonstrated good correlation between brine shrimp lethality and cytotoxicity.

The brine shrimp bioassay is a simple test. Brine shrimp are hatched in Instant Ocean dissolved in tap water, which generates a solution that approximates the constituents of sea water. The test material is handled according to its polarity and purity. Crude culture residues are tested at 10 mg, simply dissolved in the saline water used to rear the brine shrimp. The test material is dissolved in 2 ml of salt water, and an additional 2 ml of salt water containing the brine shrimp is added. The brine shrimp are counted, then recounted at various time intervals. Toxicity determined by the number of brine shrimp deaths which result from the test material, relative to a control of saline water, and a control of authentic taxol.

Biological activity of the Montana BA extract showed positive α-action (antitubulin) activity which is the comparable activity observed for authentic taxol (see references). Other biological activities observed were a positive brine shrimp test.

The members of the genus/species *Taxomyces andreanae* were cultivated with labeled nutrients to show definitively that the microbes produced taxanes it was determined that the addition of benzoic acid to the culture medium increased the amount of taxol and other taxanes.

The present invention is directed to any microbe, especially fungi, which have taxane producing characteristics, especially as described in the present invention, irrespective of their source. Such microbes are those which can produce taxol by the NMR spectrum of FIG. 1, the FAB mass spectrum of FIG. 2, the SEMS of FIGS. 4, 5 and 6 and the TEM of FIGS. 8 and 9.

In another aspect of the invention, referred to above, an appropriately labelled precursor is used to produce labelled taxol. $^{14}C$-phenylalanine is the preferred amino acid precursor, for $^{14}C$-taxol production. However, as in the above example, Na acetate-1-$^{14}C$ can be used because of its relatively low price and ability to label taxol uniformly.

The taxanes, e.g., taxol, or radiolabelled taxanes produced according to the present invention, can also be provided as a pharmaceutical composition in combination with one or more pharmaceutically acceptable inert or physiologically active diluents or adjuvants. These compositions may be prepared in any from appropriate for the administration route desired. The parenteral route and especially the intravenous route are preferred methods of administration. Compositions for parenteral administration may be aqueous or nonaqueous sterile solutions, suspension or emulsions. Propylene glycol, vegetable oils, injectable organic esters and the like, may be used as solvents or vehicles. The compositions may also contain adjuvants, wetting agents, emulsifiers or dispersants.

The compositions may also be in the form of sterile solid solutions which my be dissolved or dispersed in sterile water or any injectable sterile medium. The pharmaceutical compositions may be particularly used in the treatment of acute leukemia and solid tumors at doses know to the art, but generally in the range of between one and two milligrams per kilogram of body weight by the intravenous route for an adult. The pharmaceutical compositions should contain about 0,001 to 1.0 wt. % of effective ingredient and administered in dosage amounts known to the art for taxol.

The above microbial culture method allows for bulk compositions comprising amounts of taxanes, i.e., taxol, in bulk quantities not previously available. Previously, only small amounts of taxol, e.g., only a few hundred milligrams, have been available from extraction and other methods.

Table 1, discussed above is provided below.

TABLE 1

| Modified M-i-D Media (Filner) | | |
|---|---|---|
| | | g/l |
| Ca(NO$_3$)$_2$ | 1.20 mM | 0.28 |
| KNO$_3$ | 0.79 mM | 0.08 |
| KCl | 0.87 mM | 0.06 |
| MgSO$_4$ | 3.00 mM | 0.36 |
| NaH$_2$PO$_4$—H$_2$O | 0.14 mM | 0.02 |
| Sucrose | 87.60 mM | 30.00 |
| Ammonium Tartrate | 27.10 mM | 5.00 |
| | | mg/l |
| FeCl$_3$—6H$_2$O | 7.4 μM | 2.0 |
| MnSO$_4$ | 30.0 μM | 5.0 |
| ZnSO$_4$—7H$_2$O | 8.7 μM | 2.5 |
| H$_3$BO$_3$ | 2.2 μM | 1.4 |
| KI | 4.5 μM | 0.7 |
| pH 5.5 with 0.1M HCl | | |

TABLE 1-continued

| Modified M-i-D Media (Filner) |
|---|
| 0.25 g Yeast Extract* |

*Or omit the Yeast and supplement with:
Stock Biotin 0.5 mg/ml
Stock Thiamine 0.5 mg/ml in 40% aq. EtOH
Stock Inositol 5 mg/ml
Use 2 ml/1 of broth Table 2, discussed above is provided below.

TABLE 2

| Taxol Microbial Culture Medium | |
|---|---|
| | Grams/Liter |
| glucose | 1 |
| fructose | 3 |
| sucrose | 6 |
| KHPO$_4$—KH$_2$PO$_4$ | 1 ml of 1M pH 6.8 |
| MgSO$_4$ | .36 |
| Ca(NO$_3$)$_2$H$_2$O | .65 |
| Yeast extract | 0.5 g |
| Ca(NO$_3$)$_2$ | 1.0 mg |
| ZnSO$_4$ | 2.5 |
| MnCl$_2$ | .5 |
| FeC$_2$ | 2.0 |
| leucine | 0.1 mM |
| phenylalanine | 0.01 mM |
| NaAc | 1 mM |

Table 3, discussed above is provided below.

TABLE 3

| Comparative R$_F$ values of fungal taxol to authentic taxol and baccatin | |
|---|---|
| | Solvent System: |
| | CHCl$_3$/MeOH 78:1 v/v |
| taxol | .81 |
| fungal | .81 |
| baccatin | .75 |
| fungal baccatin | .75 |
| | CHCl$_3$ Acetonitrile 7:3 v/v |
| taxol | .47 |
| fungal taxol | .47 |
| baccatin | .50 |
| fungal baccatin | .50 |
| | Ethyl acetate isopropanol 95:5 v/v |
| taxol | .63 |
| fungal taxol | .63 |
| baccatin | .58 |
| fungal baccatin | .58 |
| | Ch$_2$Cl$_2$ Tetrahydrofuran 6:2 v/v |
| taxol | .75 |
| fungal taxol | .75 |
| baccatin | .67 |
| fungal baccatin | .67 |

TABLE 4

| Enhanced Taxol Microbial Culture Medium | |
|---|---|
| | Grams/Liter |
| glucose | 1 |
| fructose | 3 |
| sucrose | 6 |
| KHPO$_4$—KH$_2$PO$_4$ | 1 ml of 1M pH 6.8 |
| MgSO$_4$ | .36 |
| Ca(NO$_3$)$_2$H$_2$O | .65 |
| Yeast extract | 0.5 |
| Ca(NO$_3$)$_2$ | 1.0 mg |
| ZnSO$_4$ | 2.5 |
| MnCl$_2$ | 0.5 |
| FeCl$_2$ | 2.0 |
| phenylalanine | 5 mg |
| NaAc | 1 g |
| Sodium Benzoate | 10 mg-100 mg |

TABLE 5

Taxol Microbial Culture Medium
(high sugars)

| | g/liter |
|---|---|
| glucose | 1 |
| fructose | 3 |
| sucrose | 6 |
| Na acetate | 1 |
| casein amino acids | 0.5 |
| $KH_2PO_4$ pH 6.8 | 1 ml of 1M |
| vitamins | mg/liter |
| thiamine | 1 |
| biotin | 1 |
| pyridoxal | 1 |
| calcium pantothenate | 1 |
| sodium benzoate | 10–100 |
| $MgSO_4$ | 3.6 |
| $Ca(NO_3)_2$ | 6.5 |
| $Ca(NO_3)_2$ | 1 |
| $ZnSO_4$ | 2.5 |
| $MnCl_2$ | 5 |
| $FeCl_2$ | 2 |

TABLE 6

Growth and bulbil formation of *Taxomyces andreanae* on various tree species normally growing in the vicinity of *Taxus brevifolia*. All observations were recorded 1 week after inoculation with a 1.0 × 1.0 agar block supporting fungal growth.

| | Av growth from edge of agar block (cm) | | Formation of bulbils* | |
|---|---|---|---|---|
| Plant Species | Twigs/leaves | Bark | Twigs/leaves | Bark |
| *Taxus brevifolia* Nutt. Pacific Yew | 2.0 | 0.25–0.5 | heavy | heavy |
| *Betula nigra* L. River Birch | 1.0 | .75 | heavy | moderate |
| *Pinus monticola* Dougl. Western white pine | 0.1 | 0.2 | light | light |
| *Tsuga heterophylla* Rafn Sarg. Western Hemlock | 0.0 | 0.1 | none | none |
| *Pseudotsuga taxifolia* (Poir) Britt. Douglas fir | 0.1 | 0 | none | none |
| *Thuja plicata* Donn Western Red Cedar | 0.5 | 0.5 | light to moderate | heavy |
| *Picea engelmanni* Parry exEngelm. Engelmann spruce | 0.1 | 0 | moderate | none |
| *Larix occidentalis* Nutt. Western larch | 0 | 0 | none | none |

*Bulbil formation is given in terms of heavy (completely covering the area where mycelium is growing) to moderate, to light (little or sparce bulbil formation).

The fungi according to the present invention, when grown in a defined medium, use sodium benzoate 10–100 mgs/liter to recover the taxol from the medium. The fungi is preferably maintained as an inoculum source in a freshly prepared malt agar (100 mgs of benzoate/liter). The fungi do not grow well on shake culture. The optical fungal growth occurs bactosoytone 5–7 grams/liter (instead of peptone include the essential amino acids and fructose and glucose). With 10 grams sucrose, together with benzoate, vitamins and minerals as per Taxol Microbial culture medium. To further confirm the presence of taxol and baccatin in fungal preparations and extract, a culture of *T. Andreanae* was prepared by $CHCl_3$/MeOH extraction, prepared TLC on $CHCl_3$/acetonitrile 7:3 v/v followed by elution of a 1 centimeter wide area at $R_F$ 0.18–0.25. Then the residue was subjected to a micropore HPLC separation from optimum sensitivity. The study was conducted on LC/MS using a reverse phase (1 mm) × 150 mm × 5 μm particles with an Isocratic mobile phase consisting of 65 percent acetonitrile/35 percent 2 mM ammonium acetate at a flow rate of 50 microliters/minute. Subsequent analysis of two microliters of the sample prepared from 100 microliters of the dissolved sample prepared from 100 microliters of the dissolved sample yielded a peak with the retention time identical to taxol (7.85 minutes) and 6.4 minutes consistent with the pseudomolecular ion $(M + NH_4)^+$ baccatin III.

Figure 3:
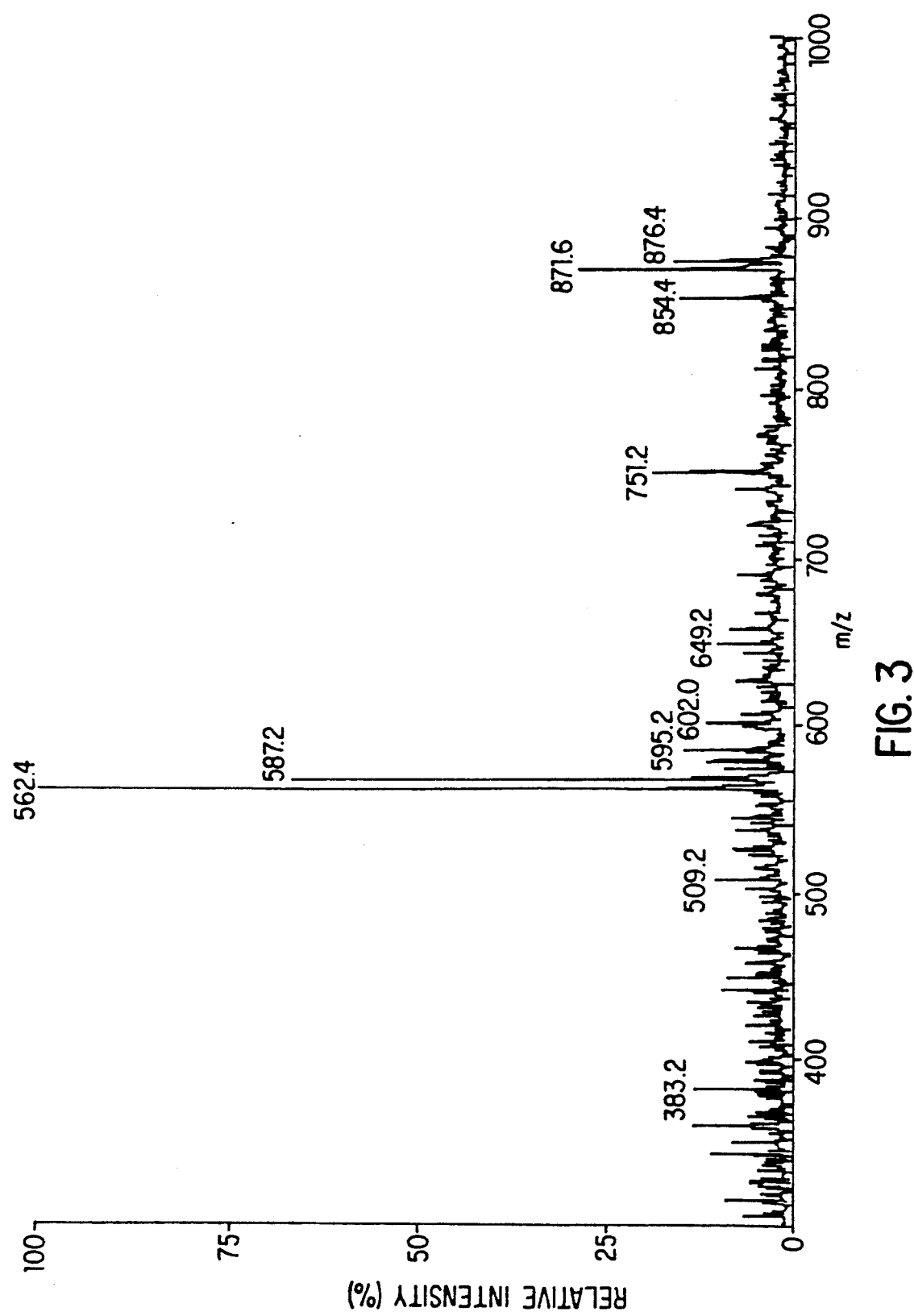
FIG. 3 shows a flow injection ion spray mass spectrum of TLC fraction RF 0.18 of fungus extract after injections of diluent wherein the low intensity ions consistent with taxol are m/z 854 and 871.

FIG. 3 illustrates the mass spectrum of the taxol eluting peak at 854–871 consistent with taxol. The amount of taxol produced in this particular medium is approximately 1 microgram/liter of the medium.

This does not represent endogenous taxol from the yew tree for several reasons. First, unless the synthetic medium contains benzoate there is substantially no taxol in the medium itself. Secondly, radio labeling experiments with phenylalanine, sodium benzoate or acetate $^{14}C$ as precursors yields radiolabel taxol. Accordingly, the experiments clearly show that the taxol is being synthesized.

To further describe the *Taxomyces andreanae* microbe, the following detailed examples are provided.

EXAMPLE 1

*Taxomyces andreanae* is a novel endophytic fungus associated with the inner bark of *Taxus brevifolia* Nutt. (Pacific Yew). This fungus has small hyphae which average 1.2 μm in diameter. It characteristically forms clumps of loosely constructed cells (bulbil-like). These clumps of various shapes and sizes typically range from about 5×5 to 16×30 μm in diameter and length. The cells in these clump average about 1.5×2.5 μm and appear to be loosely packed in the bulbi and are incapable of germination. This fungi grows rapidly on many common laboratory media, covering the plates with its mycelium in three or four days. It lacks clamp connections and dolipore septations. Its telemorph is unknown. The Taxomyces andreanae is a endophytic hyphomycete, isolated exclusively from the inner bark on small limbs of a specific yew tree in northern Montana.

The fungus species were isolated from the upper limbs of a shrub-like Pacific yew tree growing as undercover in a mature undisturbed cedar forest Flathead County, Mont. Small limbs (0.5–1.0 centimeter) were surface treated with 70 percent ethanol. The outer bark was peeled back and pieces of the white inner barks (phloem/carabium) were aseptically removed and placed on $H_2O$ agar. Hyphal tips of fungi growing from the pieces of the plant were placed on mycological agar and fungal growth was enhanced. The growth pattern of the fungus was studied on other plant species. Leaf, stem, and bark samples of various plant species growing near the tree from which this fungus was obtained were collected near the Hungry Horse dam site in the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco), e.t., potato dextrose broth agar, nutrient agar, oatmeal agar, cornmeal agar, lima bean agar, water agar, and malt agar.

EXAMPLE 2

Agar blocks having mycelia and bulbil-like structures were fixed and dehydrated as for transmission and scanning electron microscopy (SEM) (FIGS. 6, 7, 8, and 9). For SEM, the material was then critical point dried, gold coated and sputter coated, and observed with a JEOL 840A scanning electron microscope. Fungal structures were measured on SEM micrographs after critical point drying of tissues.

This drying procedure caused some shrinkage of biological structures (about 10 percent) which means that they were probably slightly larger, and the clumps of cells more tightly packed than in the living state.

EXAMPLE 3

Taxonomic Treatment and Description Taxomyces andreanae S1: Strobel, Stierle and Hess gen. et sp. nov. (FIGS. 4–9. A pure culture species was obtained of Montana BA which was named *Taxomyces andreanae* S1. This microbe producing taxane was obtained from the above screening. Its structures are described as follows.

Fungus endophyticus e cortice interiota Taxo brevifolo Nutt.; hyphae dimporphae—parvae 1.25 μm et magnae ca 3.75 μm latae et longae; bulbilus cellularum ca 1.25×2.5 μm et laxe continguus et apparenter non germinans; mycelium celiter crescens, hyphis fibulis nullis et doliporis septis nullis; telemorphus ignotus.

Figure 4:
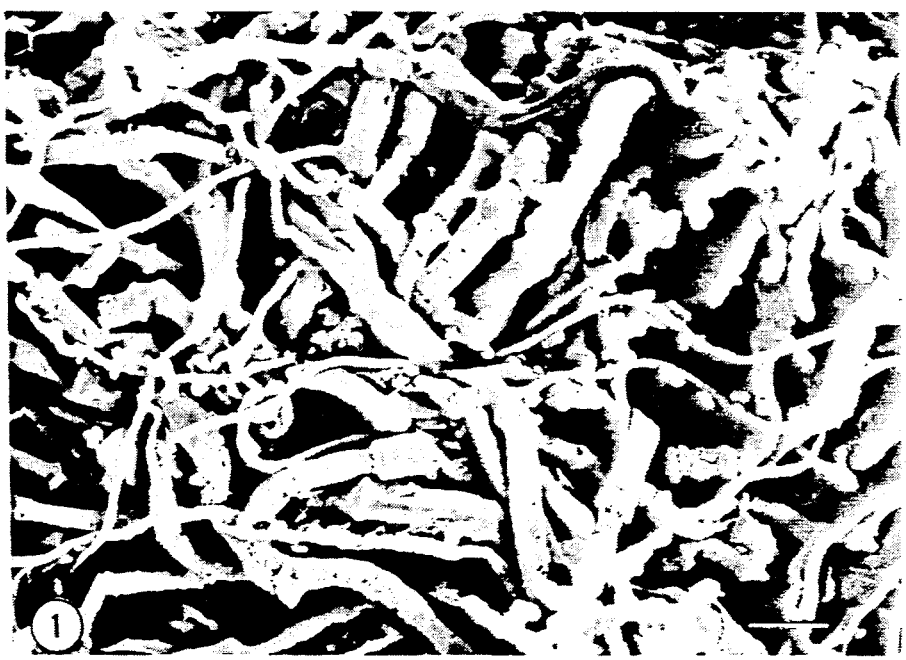
FIG. 4 shows a scanning electron micrograph of hyphae and fructigenous hyphae of T. andreanae; Bar equals 10 μm.
Figure 5:
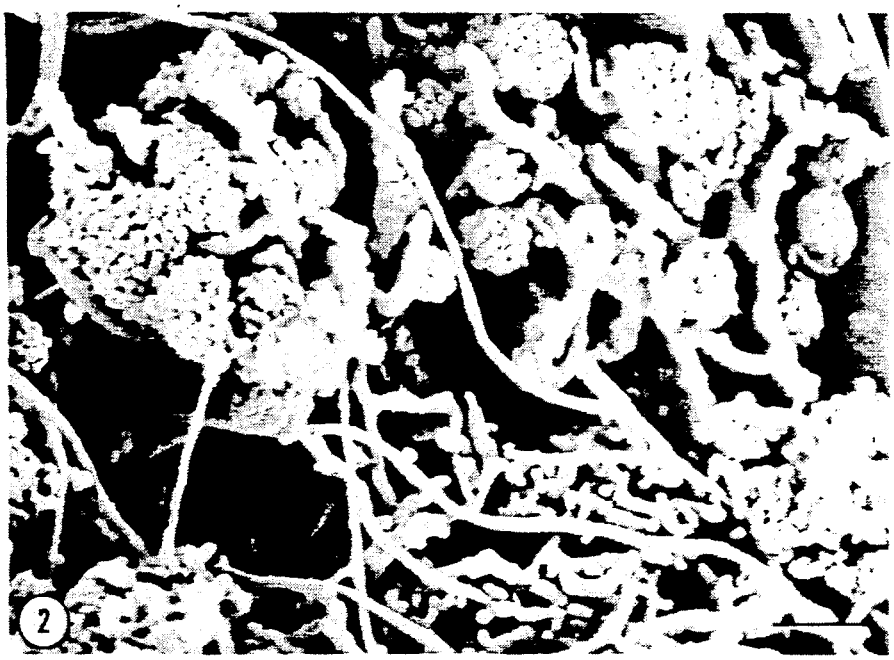
FIG. 5 shows a scanning electron micrograph of a series of various shape bulbils of *T. andreanae*; Bar=10 μm.

Mycelium superficial, composed of a network of highly branched, septate, usually hyaline, smooth walled hyphae. Smaller hyphal cells average 1.25 μm in diameter. Larger cells average 3.75 μm in diameter (FIGS. 4–5). Cells are budded from fructigenous hyphae forming clumps which vary enormously in shape from spherical to ovoid to longiform and in size from 5×5 μm in length (for elongate bulbils). Bulbil cells remaining colorless. The cells seem to be loosely packed in the bulbil and are ovoid ca. 1.5–2.5 μm and are never observed to germinate.

Figure 6:
FIG. 6 shows a scanning electron micrograph of single bulbil of *T. andreanae* illustrating the organization of the cells of the bulbil; Bar=10 μm.
Figure 7:
FIG. 7 shows the growth of *T. andreanae* on the inner bark of Pacific yew (left) and growth and bulbil formation on the leaves in small lymph fragments of *T. andreanae* (right).
Figure 9:

The "clumps" of cells in FIGS. 5 and 6 are not located on sterigmata, but seem to arise by a "budding process" (FIG. 6). Number of cells in each clump varies widely (FIGS. 5 and 6). These "clumps" are referred to as bulbils after the broad definition deBary (Comparative Morphology and Biology of Fungi, Mycetozoa and Bacteris," English Translation, Clarendon Press, Oxford), that is, "small pluricellular bodies incapable of germination". In *T. andreanae*, the cells of the bulbils, unlike most bulbilliferous fungi, appear to be loosely packed, but nevertheless connected with fibrous material (FIGS. 6, 9). These clumps of cells might also be considered as conidial masses but since germination has never been observed (in sterile H2O and nutrient broth), the clumps of cells seem to better fit the broad description of a bulbil.

Figure 8:
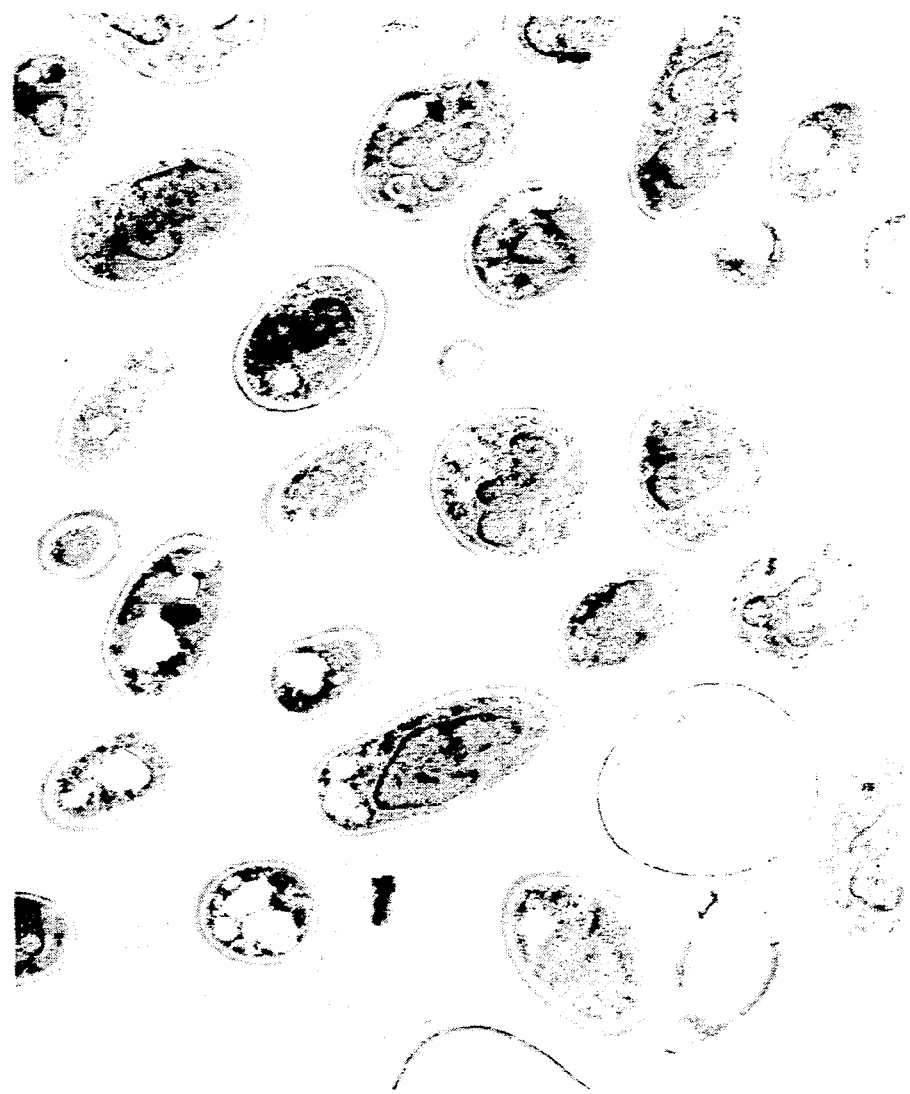
FIG. 8 shows the transmission electron micrograph of bulbil cells of *T. andreanae* illustrating a dense cytoplasm in each cell; Bar=1 μm.

Furthermore, transmission electron microscopic examination of these bulbil cells reveals that they are engorged with cytoplasmic structures including lipia bodies (FIGS. 8, 9). They also possess a bilayerea cell wall (FIGS. 8, 9). Nevertheless, these bulbils differ from the bulbils of other standard bulbilliferous fungi by lacking pigmentation, certain sclerotial-like qualities (outer rind-like cells and inner swollen cells) and in the manner of their formation.

EXAMPLE 4

A pure culture species was obtained which was named *Taxomyces andreanae* S2. The fungus species was isolated from the upper limbs of a shrub-like Pacific yew tree growing as undercover in a mature undisturbed cedar forest in Flathead County, Mont. as described in Example 1, above. Small limbs (0.5–1.0 centimeter) were surface treated with 70 percent ethanol. The outer bark was peeled back and pieces of the white inner barks (phloem/cambium) were aseptically removed and placed on $H_2O$ agar. Hyphal tips of fungi growing from the pieces of the plant were placed on mycological agar and fungal growth was enhanced.

The growth pattern of the fungus was studied on other additional plant species. Leaf, stem, and bark samples of various plant species growing near the tree from which this fungus was obtained were collected near the Hungry Horse dam site on the Flathead National Forest. Small pieces (0.5–2 cm) of leaves, stems and barks of these species were placed over four layers of cheesecloth, thoroughly dampened, and autoclaved. Agar blocks (1.0×1.0 cun) supporting fungal growth were then placed on the sterilized plant material and fungal growth was observed and measured after one week. The growth of the fungus was measured daily after placement of 0.5×0.5 cm agar blocks on standard freshly prepared agar media plates (Difco, e.g., potatol dextrose broth agar, nutrient agar, oatmeal agar, cornmeal agar, lima bean agar, water agar, and malt agar.

The fungal culture of *Taxomyces andreanae* S2, was tested and found to produce taxanes by the procedures described above.

EXAMPLE 5

A pure culture species was obtained which was named *Taxomyces andreanae* S3. The fungus species was isolated from the upper limbs of a shrub-like Pacific yew tree growing as undercover in a mature undisturbed cedar forest in Flathead County, Mont. as described in Example 1, above. Small limbs (0.5–1.0 centimeter) were surface treated with 70 percent ethanol. The outer bark was peeled back and pieces of the white inner barks (phloem/cambium) were aseptically removed and placed on $H_2O$ agar. Hyphal tips of fungi growing from the pieces of the plant were placed on mycological agar and fungal growth was enhanced.

The growth pattern of the fungus was studied on other additional plant species. Leaf, stem, and bark samples of various plant species growing near the tree from which this fungus was obtained were collected near the Hungry Horse dam site on the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco), e.g., potato dextrose broth agar, nutrient agar, oatmeal agar, cornmeal agar, lima bean agar, water agar, and malt agar.

The fungal culture of *Taxomyces andreanae* S3, was tested and found to produce taxanes by the procedures described above.

EXAMPLE 6

Cultural Characterization of *Taxomyces andreanae* S1

When an agar plug of inoculum of *Taxomyces andreanae* S1 was placed in the center of most freshly prepared agar plates enriched with various nutrients it grew so rapidly that it reached the edge of the plate in 3 days (cornmeal agar, lima bean agar, nutrient agar, malt agar, oatmeal agar). Bulbils did not form on any of these media up to 6 days after inoculation. However bulbils were noticed on the inoculum piece on the cornmeal agar after 6 days.

Some bulbils were noticed at the edge of the malt agar plate 7 days after inoculation. Numerous fluffy aerial mycelia were especially observed on malt agar and after 6–7 days the mycelium on the malt agar developed a deep reddish-brown coloration and a thick mycelial mat.

When the *Taxomyces andreanae* S1 fungus was placed on the autoclaved leaves, fragments of small limbs and bark taken from various tree species located in the geographical area of *Taxus brevifolia*, the best mycelial growth and bulbil formation occurred on Pacific yew (Table 1, FIG. 4), followed by River birch. (*Betula nigra*) (Table 1). In contrast, there was no growth on, or bulbil formation on *Larix occidentalis*, or *Tsuga heterophylla*, (Table 1). Other species differentially support weak fungal growth and bulbil formation, e.g., *Pinus monticola, Picea engelmanni* (Table 1) These observations suggest the likelihood that some host preference of *Taxomyces andreanae* S1 exists in nature and that it would be unlikely to be found in and on many species other than Taxus or Betula.

This organism appears to be a saprophyte or endophyte with the latter preferred since it was found in association with living tissue. There is no evident gross pathology of the host tree. Furthermore, attempts to use agar blocks infested with *T. andreanae* placed under the bark of yew also failed to cause any disease manifestation.

Also, the thicker hyphae ca. 3.75 μm in dia, typically extended the mycelial mat from one object (leaf or limb fragment or agar block) to another. These might be considered "exploratory hyphae". Careful study of the cultural, mycelial and bulbil characteristics in comparison to other bulbilliferous fungi nicely demonstrated the uniqueness of *Taxomyces andreanae*.

EXAMPLE 7

A fungal microbe designated as BAC-2BD-1 was isolated from the inner bark of a yew tree and grown on M-1-D medium for three weeks. Obtained were dense woolly cream colored mycelium with an irregular spreading pattern, there were no obvious fruiting. The fungal biotype was endophytic.

The cultured fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under (254 angsttoms) and sprayed with 1% vanillin in sulfuric acid. A spot with the same $R_f$ and color reaction (blue fading to brown) identical to taxol appeared.

EXAMPLE 8

A fungi microbe designated as H21 NA was isolated from the needles of a yew tree and grown on M-1-D medium for three weeks. Obtained were fine, translucent, taupe-colored mycelium with an irregular spreading pattern, fruiting structures being present as small brown-rounded bodies. The fungal biotype was parasitic.

The cultured fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angsttoms) and sprayed with 1% vanillin in sulfuric acid. A spot with the same $R_f$ and color reaction (blue fading to brown) identical to taxol appeared.

EXAMPLE 9

A fungal microbe designated as H15 NB was isolated from needles of a yew tree showing spots on the needles. This microbe was grown on M-1-D medium for three weeks. Obtained were cream colored fine mycelium, there were no obvious fruiting structures and the culture was felt-like in texture. The fungal biotype was endophytic or parasitic.

The fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angsttoms) and sprayed with 1% vanillin in sulfuric acid. A spot with the same $R_f$ and color reaction (blue fading to brown) identical to taxol appeared.

EXAMPLE 10

A fungal microbe designated as 1ND was isolated from the needles of a yew tree, grown on M-1-D medium for three weeks. Obtained were green mycelium spores identical to cladosporium sp. The fungal biotype was endophytic.

The fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angsttoms) and sprayed with 1% vanillin in sulfuric acid. A spot with the same $R_f$ and color reaction (blue fading to brown) identical to taxol appeared.

EXAMPLE 11

A fungal microbe designated as BAC-1NA-1 was isolated from the needles of a yew tree showing on the needles and grown on M-1-D medium for three weeks. Obtained were velvet-like areas on the oldest mycelial growth and there was no obvious fruiting. The fungi were ground and extracted with $CH_2Cl_2$/MeOH 10:1. The lipophilic residue was then chromatographed on 0.25 nun silica gel plates (Merck). The chromatography was conducted with chloroform/acetonitrile 7:3 v/v chloroform/methanol 7:1 v/v. The resulting plates were examined under UV (254 angsttoms) and sprayed with vanillin in sulfuric acid. A spot with the same Rf and color reaction (blue fading to brown) identical to taxol appeared.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

What is claimed is:

1. A biologically pure culture of the fungus *Taxomyces andreanae* having all the identifying characteristics of *Taxomyces andreanae* CBS 279.92.

2. The biologically pure culture of claim 1, which is isolated from a tree of the genus Taxus.

3. The biologically pure culture of claim 1, which is Taxomyces andreanae CBS 279.92.

4. The biologically pure culture of claim 1, wherein said fungus shows positive α-action antitubulin activity in a brine-shrimp assay.

5. The biologically pure culture of claim 1, wherein said fungus has a hyphae which average 1.2 μm in diameter and have bulbi which are incapable of germination.

6. The biologically pure culture of claim 1, wherein said fungus has superficial mycelium composed of a network of highly branched, septate, hyaline, smooth walled hyphae which average 1.25 μm in diameter, and larger cells which average 3.75 μm in diameter, wherein said mycelium are budded from fructigenous hyphae forming clumps which vary in shape from spherical, to ovoid, to longiform and in size from 5×5 μm in length, wherein said hyphae possess bulbil cells which lack pigmentation, are loosely packed in the bulbil, are ovoid, have a size of 1.5×2.5 μm and do not germinate.

7. The biologically pure culture of claim 2 produced by a process, which comprises,
    (a) obtaining tissue fragments from a tree of the Genus Taxus;
    (b) placing said tissue fragments on agar medium until fungal growth occurs;
    (c) placing fungal hyphae from said fungal growth on mycological agar until a culture in pure form is obtained;
    (d) transferring said fungal hyphae to a fungal lab growth medium, and growing a fungal culture;
    (e) removing at least a portion of the culture media containing the fungal culture, thoroughly grinding the mycelium, and adding a chromatographic solvent to the mixture;
    (f) obtaining a chromotograph of said fungal culture in said solvent, ad
    (g) checking the solution for the taxane reaction with vanillin-sulfuric spray, and comparing the chromatograph with one or more taxane standards selected from the group consisting of taxol, baccatin and cephalomannine.

8. The biologically pure culture of claim 2, wherein said tree is a species selected from the group consisting of *Taxus brevifolia, taxus baccata, Taxus cuspiduta, Taxus canadensis,* and *Taxus floridana*.

9. A process for producing taxol comprising the steps of
    a) culturing a fungus having all the identifying characteristics of *Taxomyces andreanae* CBS 279.92 in a medium suitable for its growth and
    b) recovering the taxol produced.

* * * * *

UNITED STATES PATENT AND TRADEMARK OFFICE
CERTIFICATE OF CORRECTION

PATENT NO. : 5,322,779
DATED : June 21, 1994
INVENTOR(S) : STROBEL ET AL.

It is certified that error appears in the above-indentified patent and that said Letters Patent is hereby corrected as shown below:

Column 1, after the title of the invention, insert the following:

-- This invention was made with support under grant number CHE-9206803 awarded by the National Science Foundation. --

Signed and Sealed this

Twentieth Day of August, 1996

Attest:

BRUCE LEHMAN

*Attesting Officer*  *Commissioner of Patents and Trademarks*